(12) United States Patent
Broers et al.

(10) Patent No.: US 12,290,051 B2
(45) Date of Patent: May 6, 2025

(54) SENSING SYSTEM FOR DETERMINING A PARAMETER OF A SET OF ANIMALS

(71) Applicant: SIGNIFY HOLDING B.V., Eindhoven (NL)

(72) Inventors: Harry Broers, 's-Hertogenbosch (NL); Marc Andre De Samber, Lommel (BE); Dragan Sekulovski, Eindhoven (NL)

(73) Assignee: SIGNIFY HOLDING, B.V., Eindhoven (NL)

( * ) Notice: Subject to any disclaimer, the term of this patent is extended or adjusted under 35 U.S.C. 154(b) by 100 days.

(21) Appl. No.: 17/928,148

(22) PCT Filed: Jun. 22, 2021

(86) PCT No.: PCT/EP2021/066894
§ 371 (c)(1),
(2) Date: Nov. 28, 2022

(87) PCT Pub. No.: WO2021/259886
PCT Pub. Date: Dec. 30, 2021

(65) Prior Publication Data
US 2023/0217901 A1 Jul. 13, 2023

(30) Foreign Application Priority Data
Jun. 25, 2020 (EP) .................................... 20182180

(51) Int. Cl.
*A01K 29/00* (2006.01)
*G06T 7/60* (2017.01)
*G06V 40/10* (2022.01)

(52) U.S. Cl.
CPC .............. *A01K 29/005* (2013.01); *G06T 7/60* (2013.01); *G06V 40/10* (2022.01); *G06T 2207/10028* (2013.01)

(58) Field of Classification Search
CPC .......... A01K 1/00; A01K 5/02; A01K 5/0291; A01K 11/006; A01K 11/008; A01K 29/00;
(Continued)

(56) References Cited

U.S. PATENT DOCUMENTS

2004/0032974 A1* 2/2004 Kriesel ................ G06V 10/145
382/110
2005/0257748 A1 11/2005 Kriesel et al.
(Continued)

FOREIGN PATENT DOCUMENTS

CH 699339 A2 * 2/2010 ............. A01D 75/20
CN 101123874 A 2/2008
(Continued)

*Primary Examiner* — Stephen R Burgdorf

(57) ABSTRACT

The invention provides a sensing system for determining a parameter of a set of animals present on a surface area, wherein the sensing system comprises: a controller; at least one range sensor having a Field-of-View to the surface area; wherein the at least one range sensor is configured to at least continually measure heights of animals of the set of animals passing the Field-of-View during a period of time, and to provide a height signal comprising said measured heights during the period of time; wherein the controller is configured to obtain said height signal, and to determine the parameter of the set of animals based on the measured heights during the period of time.

13 Claims, 4 Drawing Sheets

(58) Field of Classification Search
CPC .. A01K 29/005; A01K 39/0125; A01K 45/00;
A61B 5/0064; A61B 5/1079; A61B
5/1118; A61B 2503/40; G01S 17/08;
G06T 7/0012; G06T 7/20; G06T 7/60;
G06T 2207/10028; G06V 40/10
USPC ...................................................... 340/573.3
See application file for complete search history.

(56) References Cited

U.S. PATENT DOCUMENTS

| | | |
|---|---|---|
| 2007/0093965 A1 | 4/2007 | Harrison et al. |
| 2010/0224140 A1* | 9/2010 | Bareket ..................... G06T 7/12 |
| | | 382/110 |
| 2011/0125062 A1 | 5/2011 | Mulder |
| 2011/0126770 A1 | 6/2011 | Mulder et al. |
| 2016/0183502 A1 | 6/2016 | Tanase et al. |
| 2016/0295838 A1 | 10/2016 | Van Der Kamp et al. |
| 2018/0228587 A1 | 8/2018 | De Groot et al. |
| 2018/0242558 A1* | 8/2018 | O'Connell ............. G01G 17/08 |
| 2018/0293430 A1 | 10/2018 | Datta et al. |
| 2019/0090459 A1 | 3/2019 | Adams et al. |
| 2019/0307106 A1 | 10/2019 | Hartung et al. |

FOREIGN PATENT DOCUMENTS

| | | | | |
|---|---|---|---|---|
| JP | 2002286421 A | 10/2002 | | |
| JP | 2018520680 A | 8/2018 | | |
| NL | 2022442 A | 2/2019 | | |
| WO | 2010012431 A1 | 2/2010 | | |
| WO | 2017030448 A1 | 2/2017 | | |
| WO | WO-2020153844 A1 * | 7/2020 | ................ | A01J 5/00 |

* cited by examiner

SENSING SYSTEM FOR DETERMINING A PARAMETER OF A SET OF ANIMALS

CROSS-REFERENCE TO PRIOR APPLICATIONS

This application is the U.S. National Phase application under 35 U.S.C. § 371 of International Application No. PCT/EP2021/066894, filed on Jun. 22, 2021, which claims the benefit of European Patent Application No. 20182180.8, filed on Jun. 25, 2020. These applications are hereby incorporated by reference herein.

FIELD OF THE INVENTION

The invention relates to a sensing system for determining a parameter of a set of animals. The invention further relates to a method of determining a parameter of a set of animals, and a corresponding computer program product. The parameter may be a growth parameter or an activity parameter. The invention further relates to a lighting system.

BACKGROUND OF THE INVENTION

Agriculture has become more industrialized in modern communities. This is also the case for animal farming. The number of animals (and corresponding animal density), the associated infrastructures and the various growing methods are scaled up to achieve economically viable production of food (e.g. meat) at relatively low price levels. Monitoring the activity and/or body weight of a large population of animals is therefore a relevant parameter, e.g. to determine feeding strategies, to control growth rate, to monitor animal health & wellbeing, to plan farm logistics, etc.

For example, poultry farming is a relevant part of animal farming. The growth of poultry is thereby commonly determined by automatic scales for (broiler) chicken to step on. Such scales provide real-time weight information on the flock of chicken (after some statistical processing). The weight information may be used to obtain metrics on growth, to spot trends, and to address possible issues in animal health and wellbeing. Similar scales are seen for other sectors in animal farming.

However, a clear disadvantage of such scales is that the measured weight may be relatively inaccurate due to measurement bias, which may lead to an inaccurate input to the statistical analysis that is used to derive a weight distribution. Namely, it is known that larger birds use a scale less than smaller birds. Another disadvantage is that the scales are obtrusive, and require physical placement in a stable and interaction with the animal to measure weight. Another disadvantage is that contact between an animal and the scale may contaminate the scale, and thereby make it inaccurate or even out-of-action.

Therefore, more research is directed to monitor animals with a camera, and provide image processing techniques to extract real-time growth. Similar alternatives are proposed with 3D sensing technology. However, even though these solutions are unobtrusive, these solutions are cumbersome and are still prone to (computational) errors. Moreover, the practical implementation of these solutions is relatively (cost) expensive for only monitoring and computing the body weight of the animals. Moreover, because such technologies often require each individual animal to be clearly visible or detected, such camera or 3D sensing based technologies may not be able to easily cope with a set of animals, such as a flock, a herd, a group, a pack, etc.

SUMMARY OF THE INVENTION

It is an object of the invention to provide a sensing system, which at least alleviates the problems and disadvantages mentioned above. Thereto, the invention provides a sensing system for determining a parameter of a set of animals present on a surface area, wherein the sensing system comprises: a controller; at least one range sensor having a Field-of-View configured to be directed to the surface area; wherein each range sensor of the at least one range sensor comprises a single pixel configured to at least continually measure heights of animals of the set of animals passing the Field-of-View during a period of time, and to provide a height signal comprising said measured heights during the period of time; wherein the controller is configured to obtain said height signal, and to determine the parameter of the set of animals based on the measured heights during the period of time.

The sensing system according to the invention is enabled by the use of the range sensor having the Field-of-View to the surface area. The sensing system may be phrased as a sensor system as well, or a sensor arrangement. The set of animals is present on the surface area. Because the range sensor, with said single pixel, measures the range (or: distance) to the animals passing the Field-of-View, the range sensor is able to measure the heights of these animals relative to the surface area. The at least one range sensor may similarly measure the heights of particular body parts of these animals relative to the surface. Throughout the application, said 'range sensor measuring' may be phrased as said 'single pixel of the range sensor measuring', or said 'range sensor measuring, with the single pixel'.

Therefore, the single pixel of the range sensor at least continually measures heights of animals of the set of animals passing the Field-of-View during a period of time, and provides a height signal comprising these measured heights during the period of time. Said measuring may alternatively be continuous. The controller of the sensing system is configured to obtain this height signal. The controller may subsequently determine a parameter of the set of animals based on the measured heights during the period of time. The parameter may thereby be correlated to the measured height of the set of animals.

The present invention is thus enabled by using the at least one range sensor. Such at least one range sensor may be relatively cost efficient. For example, the range sensor may be a single-element sensor, such as a (e.g. single-pixel) Time-of-Flight (ToF) sensor. Such a range sensor provides high-performance proximity and ranging sensing. For example, an optical Time-of-Flight sensor may directly measure a distance to an object based on the time in which emitted photons are reflected.

As a result, the sensing system of the present invention is advantageous, because a parameter of a set of animals may be determined in a less cumbersome, more effective, and more cost efficient manner by using a less complicated range sensor(s) and further processing of the respective height signal. Such a parameter may for example be a growth parameter or an activity parameter.

Even further, determining various parameters of a set of animals may be difficult due to the larger number of animals in the set of animals, such as e.g. a flock of chicken in a poultry farm. The present invention advantageously solves determining a parameter of such a set of animals. For example, said parameter may be an average weight increase of the set of animals. The present invention may resolve this difficulty by determining the average weight increase based on the measured heights of the animals of the set of animals (which increase in weight may be correlated to increases in height according to animal literature). The measured heights are thereby determined by using said less complicated and cost efficient range sensor(s). Hence, the present invention is clearly beneficial for animal farming.

Animals of the set of animals may pass the Field-of-View of the at least one range sensor during the period of time. Since the set of animals may comprise a plurality of animals, the at least one range sensor may measure the animals of the plurality of animals. This allows for the sensing system to establish a (statistical) representation of the heights of the animals of the plurality of animals. For example, considering a flock of chicken, the accuracy of the measured heights (i.e. measurement errors and/or standard deviation) may be further improved with a higher number of animals in the set of animals and/or implementing more range sensors of the at least one range sensor.

Moreover, the single pixel of the range sensor may measure the heights of animals of the set of animals passing the Field-of-View during the period of time. However, the height of an animal may not be the same for the complete shape of the animal. For example, a characteristic silhouette of a chicken may comprise a higher head part, a lower carcass part, and again a higher tail part. A chicken passing the Field-of-View of a range sensor may therefore render a height signal comprising (plotted against time) a saddle shape in between two tops. The present invention may advantageously utilize such characteristic silhouettes and shapes to determine various parameters of the set of animals. For example, the head part of the chicken that is represented by the highest top, or the carcass part of the chicken that is represented by the saddle shape, may be used to determine the height and/or the average weight increase of the chicken when compared over a period of time. Moreover, the instantaneous change in height of the chicken when passing the Field-of-View may be indicative of a speed of movement of a chicken. That is: if the detected saddle shape is shorter in duration, this is indicative of the chicken moving faster through said Field-of-View.

The controller may be a standalone controller, or may be integrated in a housing together with a range sensor of the at least one range sensor. Hence, the controller may be local or distributed. The communication between the at least one range sensor and the controller may be via a wired communication means, or via wireless communication, such as Bluetooth, ZigBee, Wi-Fi, Li-Fi, VLC, RF, IR, Lo-Ra, etc.

In an embodiment, the set of animals may constitute of at least 10 animals (such as e.g. cows), or at least 100 animals (such as e.g. pigs or goats), or at least 1000 animals (such as e.g. chicken or rodent or fish), or at least 10000 animals (such as e.g. insects or shrimp or avian species).

Moreover, said parameter of a set of animals, as used throughout the application, may alternatively be defined as a condition of a set of animals.

In embodiments: The parameter may be a growth parameter. The growth parameter may be correlated to the measured heights of the set of animals. The controller may be configured to determine the growth parameter by comparing an average of the measured heights of the animals of the set of animals during a second subperiod of time with an average of the measured heights of the animals of the set of animals during a first subperiod of time.

Hence, the average of the measured heights of the animals of the set of animals during a first subperiod of time may be compared to the average of the measured heights of the animals of the set of animals during a second subperiod of time. The period of time may comprise the subperiods of time.

Said comparison allows to monitor an average increment in the measured height of the set of animals. Namely, the set of animals remains the same sample. An average of the measured heights of the animals (i.e. the sample) may subsequently be determined for two different measurement periods in time (i.e. the measurements performed respectively in the first and second subperiod of time). This enables to determine an increment (or: delta) in height (e.g. increase or decrease). Consequently, the determined increment (or: delta) in height may be statistically relevant for the set of animals, as the set (or: sample) comprises sufficient animals passing the Field-of-View of the at least one range sensor during the respective subperiods of time. Said 'set' may alternatively be phrased as 'population'.

Since the measured height may be correlated to the growth parameter, an average increment associated to the growth parameter may be determined. The size of the animal may e.g. be correlated to the height of an animal. The weight of the animal may e.g. also be correlated to the height of an animal. These correlations are common in animal literature. Hence, in an embodiment, the growth parameter may be (at least) one of: an average increment of the height of the set of animals, an average increment of the size of the set of animals, or an average increment of the weight of the set of animal. In aspects, the growth parameter may be any combination of the above mentioned three average increments.

For example, taking a simplified example for convenience, the at least one range sensor may measure the height of animals of a population of animals passing the Field-of-View during a first subperiod of time. For the measurements taken during the first subperiod of time, the measured heights of the plurality of animals may for example be determined to be on average twenty centimeters. These heights may thereby be in aspects only the maximum heights (e.g. the head of the chicken) in the height signal (i.e. the tops). This may indicate that an animal of the population of animals is on average twenty centimeters in height. Subsequently, the at least one range sensor may measure the height of animals of the same population of animals passing the Field-of-View during a second period of time. For the measurements taken during the second subperiod of time, the measured heights of the plurality of animals may for example be determined to be on average thirty centimeters. This may indicate that an animal of the population of animals is on average thirty centimeters in height. The difference between the two subperiods of time is thus ten centimeters in height. Hence, the population of animals comprises an average increment in height of ten centimeters. Hence, the sensing system may thereby also determine the average increment of weight of the set of animals based on the average increment in height of ten centimeters, since weight may be correlated to the height of the animals as mentioned before.

In another example, the growth parameter may be indicative of end-of-growth. Namely, the controller may be configured to determine end-of-growth of the set of animals when an average of the measured heights of the animals of the set of animals during a second subperiod of time differs at most within a predetermined threshold from an average of the measured heights of the animals of the set of animals during a first subperiod of time. Said predetermined threshold may for example be at most a 2% difference between said averages of the measured heights, alternatively at most a 1% difference. This may indicate that the set of animals is no longer growing, hence end-of-growth is achieved. This may be advantageous in animal farming, because e.g. the time of harvest of the set of animals may be determined. Phrased differently: the controller may be configured to determine end-of-growth of the set of animals when an average of the measured heights of the animals of the set of animals during a second subperiod of time is no more than 2% (alternatively 1%) different to an average of the measured heights of the animals of the set of animals during a first subperiod of time.

Yet alternatively, in aspects, the growth parameter may be indicative of a growth-spurt. Namely, the controller may be configured to determine the growth-spurt of the set of animals when an average of the measured heights of the animals of the set of animals during a second subperiod of time differs at least beyond a predetermined threshold from an average of the measured heights of the animals of the set of animals during a first subperiod of time. Said predetermined threshold may for example be at least a 10% difference between said averages of the measured heights, alternatively at least a 20% difference. This may indicate that the set of animals is growing too fast, hence have a growth-spurt. Detecting such a growth-spurt may be advantageous in animal farming, because it may indicate e.g. a surplus of feed, or e.g. a wrong growth lighting recipe (as the animals are growing faster than planned), or e.g. be relevant for logistics of the animal farm, or e.g. be relevant for animal wellbeing not to grow the animals too fast.

In other aspects: The parameter may be a growth parameter. The growth parameter may be correlated to the measured body shape of the set of animals. The controller may be configured to determine the growth parameter by comparing an average of the measured body shape of the animals of the set of animals during a second subperiod of time with an average of the measured body shape of the animals of the set of animals during a first subperiod of time. Thereby, the body shape of animals may be measured by means of a multi-pixel range sensor, wherein the thickness of the animal is defined by (or: correlated to, or: silhouetted by, or: outlined by) the pixels defining a height, and hence not by the pixels defining a floor level. The body shape may alternatively be a thickness. Hence, the sensing system could extract from the average shape if the set of animals (e.g. the flock of chicken) is representing on average skinny animals or animals having much 'fat on the bones'. Said multi-pixel range may thereby also be defined by separate single-pixel range sensors arranged in an array.

In embodiments: The parameter may be an activity parameter of the set of animals. The activity parameter may be correlated to the duration of the measured heights of the set of animals. The controller may be configured to determine the activity parameter of the set of animals by comparing an average duration of the measured heights of the animals of the set of animals during a second subperiod of time with an average duration of the measured heights of the animals of the set of animals during a first subperiod of time. More specifically: Said average duration of the measured heights of the animals being the average duration of how long a respective measured height of an animal lasts in time taking into account all respective measurements made.

Hence, the average duration of the measured heights of the animals of the set of animals during a first subperiod of time may be compared to the average duration of the measured heights of the animals of the set of animals during a second subperiod of time. The period of time may comprise the subperiods of time. Since an average is taken over a respective subperiod of time, it is not necessary that each animal of the set of animals passes through the Field-of-View of the at least one range sensor.

Said comparison allows to monitor an average increment in the duration of the measured height of the set of animals. Namely, the set of animals may remain the same sample. An average duration of the measured heights of the animals (i.e. the sample) may subsequently be determined for two different measurement periods in time (i.e. the measurements performed respectively in the first and second subperiod of time). This enables to determine an increment (or: delta) in duration of a particular measured height. Consequently, the determined increment (or: delta) in duration of the height may be statistically relevant for the set of animals, as the set (or: sample) comprises sufficient animals passing the Field-of-View of the at least one range sensor during the respective subperiods of time. Said 'set' may alternatively be phrased as 'population'.

Since the duration of the measured height may be correlated to the activity parameter, which duration of the measured height may substantially be indicative of the velocity (or: speed) of the animals, different (minor/major motion) properties associated to the activity parameter may be determined. The activity of an animal itself may e.g. be correlated to the average duration of the measured height of an animal. The locomotion of an animal may e.g. also be correlated to the average duration of the measured height of an animal. These correlations are common in animal literature. Hence, in an embodiment, the activity parameter may be (at least) one of: an activity of the set of animals, a rate of locomotion of the set of animals, or a type of locomotion of the set of animals. In aspects, the activity parameter may be any combination of the above mentioned activity, rate and type.

For example, taking a simplified example for convenience, the at least one range sensor may measure the height of animals of a population of animals passing the Field-of-View during a first subperiod of time. For the measurements taken during the first subperiod of time, the duration of the measured heights of the plurality of animals may for example be determined to be on average two seconds. This may indicate that an animal of the population of animals on average takes on average two seconds to pass the Field-of-View. Subsequently, the at least one range sensor may measure the height of animals of the same population of animals passing the Field-of-View during a second period of time. For the measurements taken during the second subperiod of time, the duration of the measured heights of the plurality of animals may for example be determined to be on average a single second. This may indicate that an animal of the population of animals on average takes a single second to pass the Field-of-View. Hence, the population of animals is on average moving faster in the second subperiod of time compared to the first subperiod of time. Hence, the sensing system may thereby determine a rate of locomotion of this population of animals (e.g. speed value); or even the type of locomotion (e.g. running, walking, or standing still); or even determine or derive the activity of the animals (e.g. eating, mating, fluffing, or resting).

Hence, in an embodiment, the activity of the set of animals may comprise one of: sleeping, resting, eating or moving. The activity may alternatively be mating. Hence, in an embodiment, the type of locomotion of the set of animals may comprise one of: sitting, walking, running, laying, or having stress.

In an embodiment, the set of animals may be one of a flock of chicken, a herd of livestock, a group of pigs, a colony of terrestrial insects, or a population of crustaceans, or aquatic animals. Said chicken may be hens, chicks, broilers, roosters, turkeys. The set of animals may also be a flock of other poultry or other avian species. Said livestock may be cows, sheep, horses, bulls, camels. Said pigs may be bores, swine's, suckling's. The set of animals may be a group of other terrestrial animals, such as dogs, cats, rabbits, minks, crocodiles. Said terrestrial insects may be insects suited for protein production. The set of animals may further comprise fish, shrimp, or rodents. The set of animals may comprise a single (or same) type of animals.

In an embodiment, the at least one range sensor may be one of: a single-pixel Time-of-Flight sensor, a multi-pixel Time-of-Flight sensor, an infrared range sensor, a FMCW radar sensor, an ultrasound range sensor, a LIDAR.

The at least one range sensor may be a 4×4 pixel Time-of-Flight sensor, or a 8×8 pixel Time-of-Flight sensor. The at least one range sensor may comprise a single pixel. The at least one range sensor may be configured to comprise multiple pixels, and configured to read out only a single pixel during the measurements of the present invention. In an embodiment, the Field-of-View of the at least one range sensor may be less than 5 cm$^2$. Such an embodiment may be advantageous to obtain more accurate measurements of a flock in e.g. poultry farms, as the Field-of-View less than 5 cm$^2$ may be small enough to fit at least part of a single animal in the Field-of-View at a time. This may be particularly suited for poultry. Other sizes of the Field-of-View may be similarly envisioned for other groups of animals.

In an embodiment, the sensing system may be arranged in the surface area, wherein the surface area comprises a feeding area, wherein the Field-of-View of a range sensor of the at least one range sensor is configured to be directed to the feeding area. Such an embodiment may be advantageous, because the feeding area may be an area in which an animal is known to be in a particular predefined body posture, e.g. on their feet. By having a range sensor of the at least one range sensor monitoring such a feeding area, the measured height may be attributed to an animal in that particular predefined body posture, i.e. e.g. on their feet, thereby facilitating the determination of the measured heights and associated parameter of the set of animals.

In an embodiment, the sensing system may comprise an array of electric devices; wherein each electric device of the array of electric devices may comprise a respective range sensor of the at least one range sensor. Moreover, in aspects thereof, each respective range sensor may have a respective Field-of-View to the surface area; wherein each respective range sensor may be configured to at least continually measure heights of animals of the set of animals passing the respective Field-of-View during a period of time, and to provide a respective height signal comprising said measured heights during the period of time; wherein the controller may be configured to obtain each respective height signal, and determine the parameter of the set of animals based on the measured heights during the period of time.

In an embodiment, the array of electric devices may comprise an array of lighting devices. Such an embodiment may be advantageous, because the lighting system of an animal farm may be organized in a grid and/or located at positions substantially covering the location of the set of animals. Therefore, having the at least one range sensor associated with the array of lighting devices may enable an advantageous coverage for such sensors to monitor the set of animals.

In an embodiment, the controller may be configured to control an electric device upon determining the parameter. The electric device may for example be a lighting device, a speaker, a HVAC device, a fodder device, a watering device, a scent diffuser, a fan, an electric door, a heater device, a cooler device, a radiofrequency emitting device, a sensor device, a user interface device, a cloud, a server device. Such embodiment is advantageous, as the electric device may be controlled based on the determined parameter. If the parameter may be an activity parameter such as the type of locomotion indicative of the set of animals having stress, then the electric device may be controlled to soothe the set of animals determined to be having stress. For example, the electric device may be a speaker emitting soothing sounds, or a HVAC system providing cooler air to reduce heat stress in the set of animals. Other examples may be similarly envisioned.

In an embodiment, the electric device may be a lighting device, wherein the controller is configured to control the lighting device to provide a lighting characteristic upon determining the parameter, wherein the lighting characteristic is at least one of: intensity, color, color temperature, modulation, light pattern, light scene, light recipe, light schedule.

It is a further object of the invention to provide an improved method, which at least alleviates the problems and disadvantages mentioned above. Thereto, the invention further provides a method of determining a parameter of a set of animals present on a surface area, wherein the method comprises: at least continually measuring heights of animals of the set of animals passing a Field-of-View of a range sensor during a period of time with a single pixel of the range sensor; providing a height signal comprising said measured heights during the period of time; obtaining said height signal and determining the parameter of the set of animals based on the measured heights during the period of time. The advantages and/or embodiments applying to the sensor system according to the invention may also apply mutatis mutandis to the method according to the invention.

In an embodiment, the parameter may be a growth parameter; wherein the growth parameter may be correlated to the measured heights of the set of animals; wherein the method according to the invention (further) comprises: determining the growth parameter by comparing an average of the measured heights of the animals of the set of animals during a second subperiod of time with an average of the measured heights of the animals of the set of animals during a first subperiod of time.

In an embodiment, the parameter may be an activity parameter; wherein the activity parameter may be correlated to the duration of the measured heights of the set of animals; wherein the method according to the invention (further) comprises: determining the activity parameter of the set of animals by comparing an average duration of the measured heights of the animals of the set of animals during a second subperiod of time with an average duration of the measured heights of the animals of the set of animals during a first subperiod of time.

In an embodiment, the sensing system may comprise an array of electric devices; wherein each electric device of the array of electric devices comprises a respective range sensor of the at least one range sensor; wherein each respective range sensor has a respective Field-of-View to the surface area; wherein the method according to the invention (further) comprises: at least continually measuring heights of animals of the set of animals passing the respective Field-of-View during a period of time; providing a respective height signal comprising said measured heights during the period of time; obtaining each respective height signal and determining the parameter of the set of animals based on the measured heights during the period of time.

The invention further relates to a computer program product. Hence, the invention provides a computer program product for a computing device, the computer program product comprising computer program code to perform a method according to the invention when the computer program product is run on a processing unit of the computing device.

Thus, aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

It is a further object of the invention to provide an improved lighting system, which at least alleviates the problems and disadvantages mentioned above. Thereto, the invention provides a lighting system comprising a lighting device and the sensing system according to the invention, wherein the controller is configured to control a lighting characteristic of the lighting device upon determining said parameter.

In an embodiment, the lighting characteristic may be at least one of: intensity, color, color temperature, a light spectrum, a light pattern, a light modulation, a light scene, a light recipe, a light schedule, a polarization.

In an embodiment, wherein the controller may be configured to control the lighting device to adapt a period of a light-and-dark schedule upon determining an average increment of the weight of the set of animals. The controller may also additionally or alternatively be configured to control the lighting device to adapt a light recipe to control an animal activity, to control a farm activity (such as functional lighting for harvest actions, etc.), to control an animal behavior (such as e.g. aggression when average movement of the set of animals is determined to be increased).

In aspects, the invention may not be limited to a set of animals, but may similarly advantageously determine a parameter (such as an activity parameter) for a single animal. Hence, the invention provides a sensing system for determining a parameter of an animal present on a surface area, wherein the sensing system comprises: a controller; at least one range sensor having a Field-of-View to the surface area; wherein the at least one range sensor is configured to at least continually measure height of the animal passing the Field-of-View during a period of time, and to provide a height signal comprising said measured height during the period of time; wherein the controller is configured to obtain said height signal, and to determine the parameter of the animal based on the measured height during the period of time. The advantages and/or embodiments applying to the sensor system according to the first aspect invention may also apply mutatis mutandis to this aspect of the invention.

The parameter may be a growth parameter. The growth parameter may be correlated to the measured height of the animal. The controller may be configured to determine the growth parameter by comparing an average of the measured height of the animal during a second subperiod of time with an average of the measured height of the animal during a first subperiod of time. The growth parameter may be one of: an average increment of the height of the animal, an average increment of the size of the animal, or an average increment of the weight of the animal. The parameter may be an activity parameter of the animal. The growth parameter may be correlated to the duration of the measured height of the animal. The controller may be configured to determine the activity parameter of the animal by comparing an average duration of the measured height of the animal during a second subperiod of time with an average duration of the measured height of the animal of the animal during a first subperiod of time. The activity parameter may be one of: an activity of the animal, a rate of locomotion of the animal, or a type of locomotion of the animal. The activity of the animal may comprise one of: sleeping, resting, eating or moving. The type of locomotion of the animal may comprise one of: sitting, walking, running, laying, or having stress.

In aspects, the invention provides a sensing system for determining a parameter of a set of animals present on a surface area at a position, wherein the sensing system comprises: a controller; at least one range sensor having a Field-of-View to the surface area and positioned at a respective location; wherein the at least one range sensor is configured to at least continually measure heights of animals of the set of animals passing the Field-of-View during a period of time at said respective location, and to provide a height signal comprising said measured heights during the period of time at said respective location; wherein the controller is configured to obtain said height signal and obtain each respective location of the at least one range sensor, and to determine the parameter of the set of animals at a position based on the measured heights during the period of time at each respective location of the at least one range sensor. When the number and distribution of the at least one range sensor is sufficient to cover a large part of the surface area, then the sensing system may provide a heat map of measured height signals, and determine average changes of these measured heights during the period of time (as defined before in this application). This may allow the sensing system to determine the parameter of the set of animals, but also provide a spatial (e.g. X,Y) distribution (of the increment) of this parameter during the period of time. The advantages and/or embodiments applying to the sensor system according to the first aspect invention may also apply mutatis mutandis to this aspect of the invention.

In aspects, the invention provides a sensing system for determining a parameter of a set of animals present on a surface area, wherein the sensing system comprises: a controller; at least one range sensor having a Field-of-View configured to be directed to the surface area; wherein each range sensor of the at least one range sensor is configured to at least continually measure heights of animals of the set of animals passing the Field-of-View during a period of time, and to provide a height signal comprising said measured heights during the period of time; wherein the controller is configured to obtain said height signal, and to determine the parameter of the set of animals based on the measured heights during the period of time.

In an embodiment thereof, each range sensor of the at least one range sensor comprises a single pixel configured to at least continually measure heights of animals of the set of animals passing the Field-of-View during a period of time, and to provide a height signal comprising said measured heights during the period of time.

BRIEF DESCRIPTION OF THE DRAWINGS

The invention will now be further elucidated by means of the schematic non-limiting drawings.

DETAILED DESCRIPTION OF THE EMBODIMENTS

Figure 1:
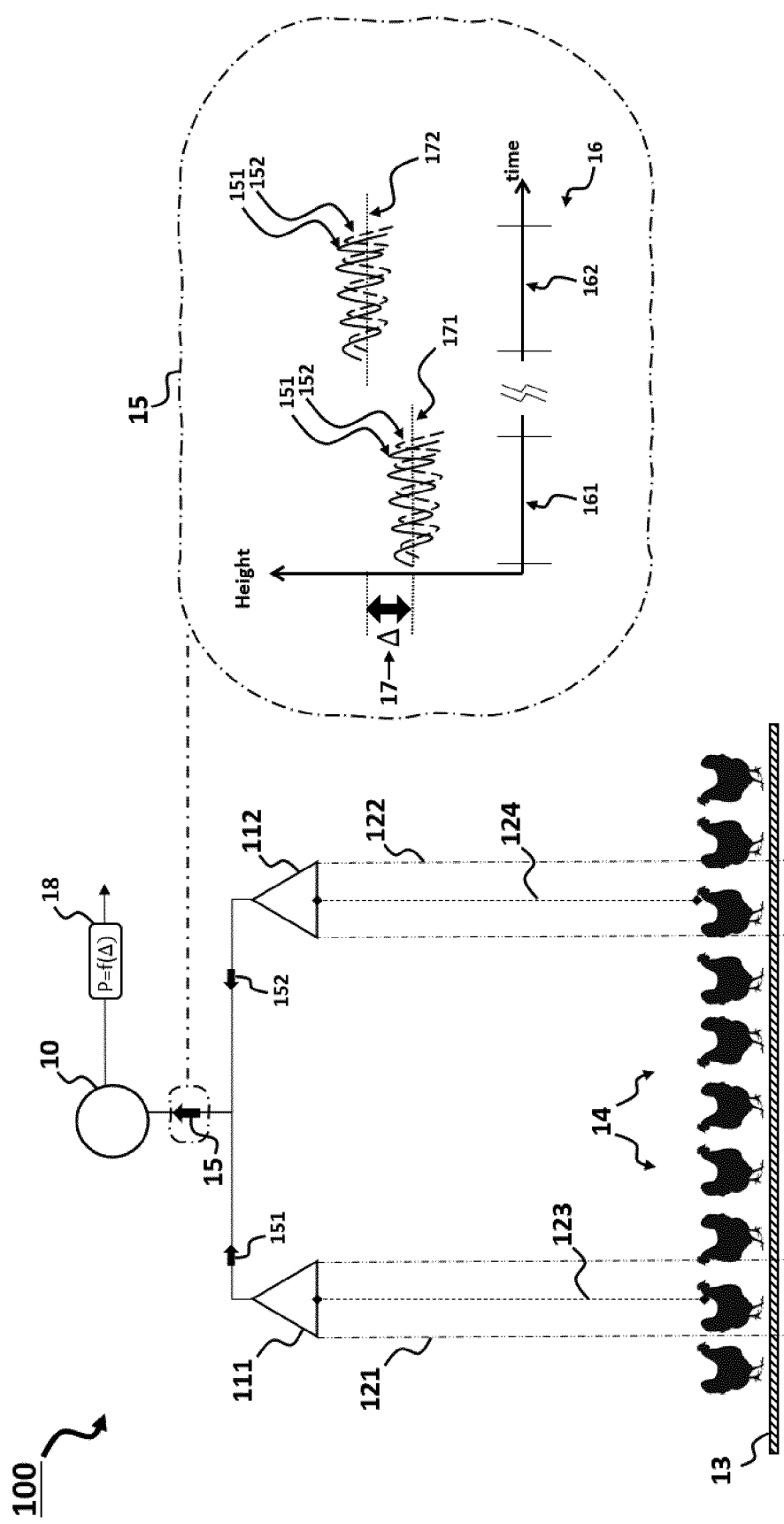
FIG. 1 depicts schematically an embodiment of a sensing system according to the invention.

FIG. 1 depicts schematically, by non-limiting example, an embodiment of a sensing system 100 according to the invention. The sensing system 100 is installed in an animal farm comprising a set of animals 14. Here, the animal farm is producing poultry, in particular chicken. Therefore, the animal farm comprises a flock of chicken 14. The flock of chicken 14 is present on a surface area 13 of the animal farm. The flock of chicken 14 is bounded by the animal farm, but free to move around on the surface area 13. The surface area 13 may be the floor (or: bedding) of the farm (or: stable). The flock of chicken 14 may be considered to demonstrate a common vivid (or: substantially random, or: instinctive) movement in the animal farm.

Alternatively, the animal farm may be another venue comprising the set of animals. Alternatively, said set of animals may be another set of animals provided before in the present application, such as a group of pigs, or a herd of sheep, or livestock, or horse, or insects.

The sensing system 100 is arranged to determine a parameter 18 of the set of animals 14. Therefore, the sensing system 100 comprises a controller 10 and at least one range sensor 111, 112. The present embodiment, as depicted in FIG. 1, but not limited in any sense to the number, comprises a first range sensor 111 and a second range sensor 112. Thus alternatively, the at least one range sensor may be a single range sensor. In a different, but similar embodiment (not depicted), the sensing system may therefore comprise only one range sensor, such as range sensor 111 only, while the other features described below are mutatis mutandis applied.

Referring to FIG. 1, the range sensors 111, 112 are a single-pixel optical Time-of-Flight sensors. Such a Time-of-Flight sensor provides high-performance proximity and ranging sensing. This Time-of-Flight sensor may directly measure a distance to an object based on the time in which emitted photons are reflected. Thus, the first range sensor 111 is configured to measure the distance 123 to an object (i.e. a chicken of the flock of chicken) in its (single-pixel) Field-of-View (or: detection area). Thus, the second range sensor 112 is configured to measure the distance 124 to an object (i.e. a chicken of the flock of chicken) in its (single-pixel) Field-of-View (or: detection area). Alternatively, the at least one range sensor may be one of: a multi-pixel Time-of-Flight sensor, an infrared range sensor, a FMCW radar sensor, an ultrasound range sensor, or LIDAR.

The controller 10 is in wired communication with the first range sensor 111 and the second range sensor 112. This communication may alternatively be wireless, via a wireless communication modality provided before in the present application. The controller 10 is thereby separate from the at least one sensor 111, 112. Alternatively, the controller 10 may be part of at least one of the at least one range sensor, such as a local controller or a distributed controller.

Still referring to FIG. 1, the at least one range sensor comprises (or: has) a Field-of-View to the surface area 13. Thus, the first range sensor 111 and the second range sensor 112 comprise a respective first Field-of-View 121 and a respective second Field-of-View 122 to the surface area 13.

The various chicken of the flock of chicken 14 may pass both Field-of-Views 121, 122 of the range sensors 111, 112 during a period of time 16. Both the first range sensor 111 as well as the second range sensor 112 are at least continually measuring heights 151, 152 of the chicken of the flock of chicken 14 passing the respective Field-of-View 121, 122 during the period of time 16. The height of the chicken may be derived from the measured distance 123, 124 by known processing means. Thereby, the first range sensor 111 provides a height signal comprising said measured heights 151 during the period of time 16, and the second range sensor 112 provides a height signal comprising said measured heights 152 during the period of time 16. (In the alternative embodiment mentioned above comprising a sensing system with only one range sensor, the height signal would therefore also be a single height signal). Here, these two height signals are considered as the (aggregated) height signal 15 according to the invention. Since the flock of chicken 14 may comprise a plurality of chicken, the at least one range sensor 111,112 may measure various and many chicken of the flock of chicken 14. This allows for the sensing system to establish a (statistical) representation of the heights of the chicken of the flock of chicken 14.

In examples, the Field-of-View may comprise a dedicated size, which may for example be less than 5 cm$^2$. In examples, the surface area may also comprise a feeding area, wherein a range sensor of the at least one range sensor may have a Field-of-View to the feeding area. This may be advantageous, because the feeding area may be an area in which the chicken is known to be on their feet, and it may be more accurately ensured that the standing height of the chicken is measured.

Still referring to FIG. 1, as mentioned, the at least one range sensor 111, 112 provides a height signal 15 comprising said measured heights 151, 152 during the period of time 16. The controller 10 obtains said height signal 15 (either receives or retrieves, from e.g. server to which the at least one range sensor transmits the measurement data). The controller 10 further determines the parameter 18 of the flock of chicken 14 based on the measured heights 151, 152 during the period of time 16.

More specifically, the parameter 18 is a growth parameter. Namely, the growth parameter is an average increment of the weight of the flock of chicken 14. The growth parameter is correlated to the measured heights 151, 152 of the flock of chicken 14. That is: weight increase may be determined in literature via height increase. Thus, the controller 10 determines the growth parameter (i.e. the average increment of the weight of the flock of chicken 14) by comparing an average 172 of the measured heights 152 of the animals of the flock of chicken 14 during a second subperiod of time 162 with an average 171 of the measured heights 151 of the animals of the set of animals 14 during a first subperiod of time 161. This comparison namely renders the average increment 17 (or: delta) in height of the flock of chicken 14, which may thus be correlated to the average increment in weight increase of the flock of chicken 14. Alternatively, said growth parameter may be an average increment of the size of the set of animals, or an average increment of the height of the set of animals itself.

As a result, the sensing system 100 determines the growth parameter 18, which is the average increment of the weight of the flock of chicken 4, by means of the height signal 15 measured by the respective range sensors 111, 112. This is a less cumbersome, more effective, and more cost efficient manner of determining the growth parameter 18 of the (vivid and continuously moving) flock of chicken 14. Hence, the present invention is clearly beneficial for animal farming, and in particular to poultry farming.

In an embodiment, not depicted, the embodiment depicted in FIG. 1 is provided, but wherein the sensing system comprises an array of two lighting devices. The first lighting device thereof comprises the first range sensor. The second lighting device thereof comprises the second range sensor. The lighting device is thereby a luminaire with a housing, and the respective range sensor is housed within the same housing. The luminaires may illuminate the surface area with a lighting characteristic. The controller may then be configured to control the first and/or second lighting device to provide a lighting characteristic upon determining the growth parameter. The lighting characteristic is at least one of: intensity, color, color temperature, modulation, light pattern, light scene, light recipe, light schedule.

Figure 2:
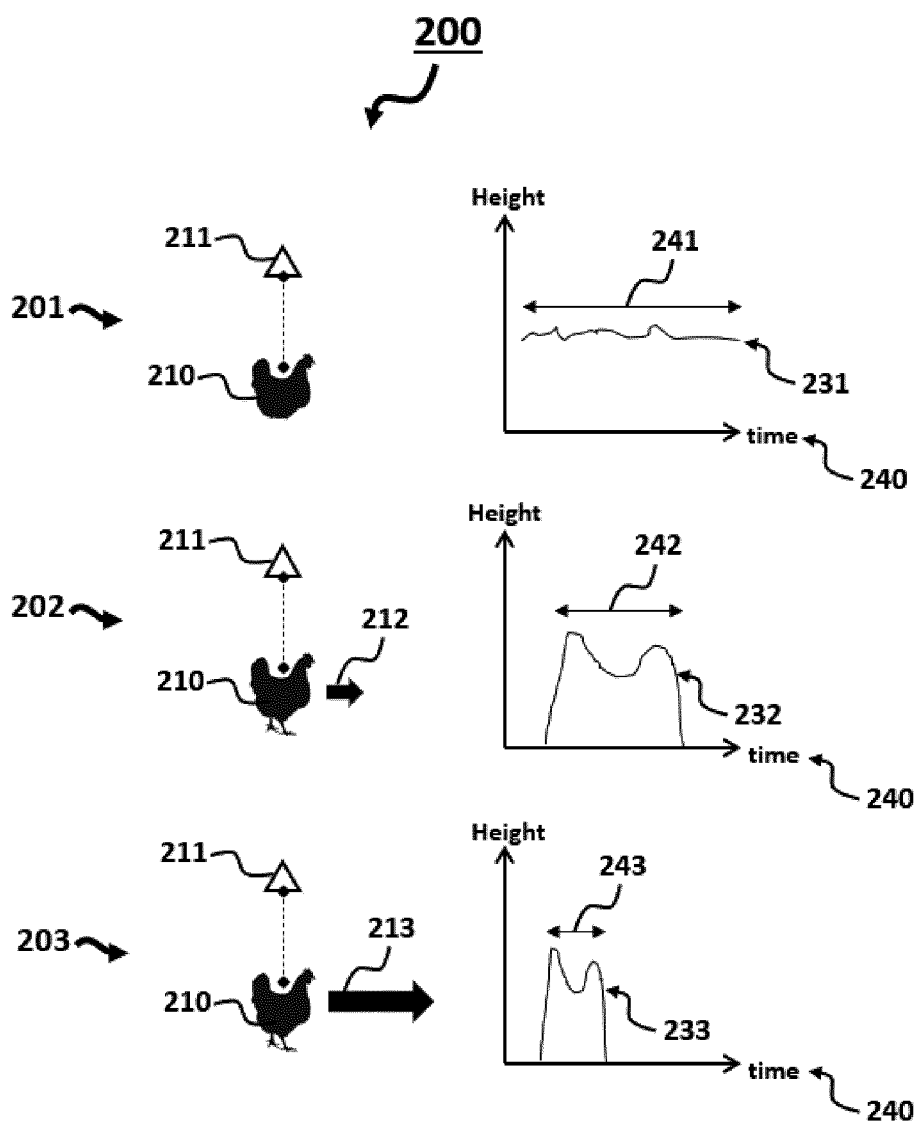
FIG. 2 depicts schematically a set of height signals of a chicken in the Field-of-View of a range sensor according to the invention.

FIG. 2 depicts schematically, by non-limiting example, a set 200 of height signals of a chicken 210. The set 200 of height signals of the chicken 210 are measured with a range sensor 211 according to the invention. The chicken 210 is namely in the Field-of-View of this range sensor 211 or passes said Field-of-View at a particular velocity. The range sensor 211 is a single-pixel optical Time-of-Flight sensor, but may alternatively be a multi-pixel Time-of-Flight sensor, an infrared range sensor, a FMCW radar sensor, an ultrasound range sensor. The range sensor 211 is configured to measure the distance to the chicken 210, thereby configured to measure the height of the chicken 210 relative to the surface area (not depicted) the chicken 210 is present. This may for example be a stable floor. The range sensor 211 is configured to measure the height of the chicken 210 during a period of time 240, Referring to FIG. 2, in a first situation 201, the chicken 210 is resting and sitting within the Field-of-View of the range sensor 211 during the period of time 240. In the first situation 201, the measured height 231 of the chicken is therefore substantially constant over the period of time 240. The duration 241 of the measured height 231 is therefore a relatively long duration, for example one hour. In case multiple chicken of a flock of chicken exposes this (resting and sitting) behavior, then an average duration of the measured height 231 may also be on average such a relatively long duration.

Referring to FIG. 2, in a second situation 202, the chicken 210 is passing (or: moving in) the Field-of-View of the range sensor 211 during the period of time 240. The measured height 232 of the chicken 210 therefore renders a characteristic height signal over the period of time 240. The characteristic height signal is thereby a saddle-shape between two tops, corresponding to the head, carcass and tail of the chicken. In the second situation 202, the velocity 212 of the chicken 210 is relatively slow, because for example the chicken may be feeling comfortable. The duration 242 of the measured height 232 is therefore a relatively medium duration, for example one second. In case multiple chicken of a flock of chicken exposes this (slow velocity) behavior, then an average duration of the measured height may also be on average such a relatively medium duration.

Referring to FIG. 2, in a third situation 203, the chicken 210 is passing (or: moving in) the Field-of-View of the range sensor 211 during the period of time 240. The measured height 233 of the chicken 210 therefore renders a characteristic height signal over the period of time 240. The characteristic height signal is thereby a saddle-shape between two tops, corresponding to the head, carcass and tail of the chicken. In the third situation 203, the velocity 213 of the chicken 210 is relatively fast, because for example the chicken may be feeling stress. The duration 243 of the measured height 233 is therefore a relatively short duration, for example halve a second. In case multiple chicken of a flock of chicken exposes this (high velocity) behavior, then an average duration of the measured height may also be on average such a relatively short duration.

Hence, still referring to FIG. 2, the height signals 231, 232, 233 corresponding to the three different situations 201, 202, 203 may be indicative of an activity parameter of the chicken 210; such as the resting, normal comfortable behavior, and stress. The sensing system according to the invention may determine an activity parameter by analyzing the measured height of the chicken 210 during a period of time 240. This analysis may mutatis mutandis be applied to at least one range sensor, and to a set of chicken, such as a flock of chicken. This may render average values indicative of an average behavior of the flock of chicken.

Figure 3:
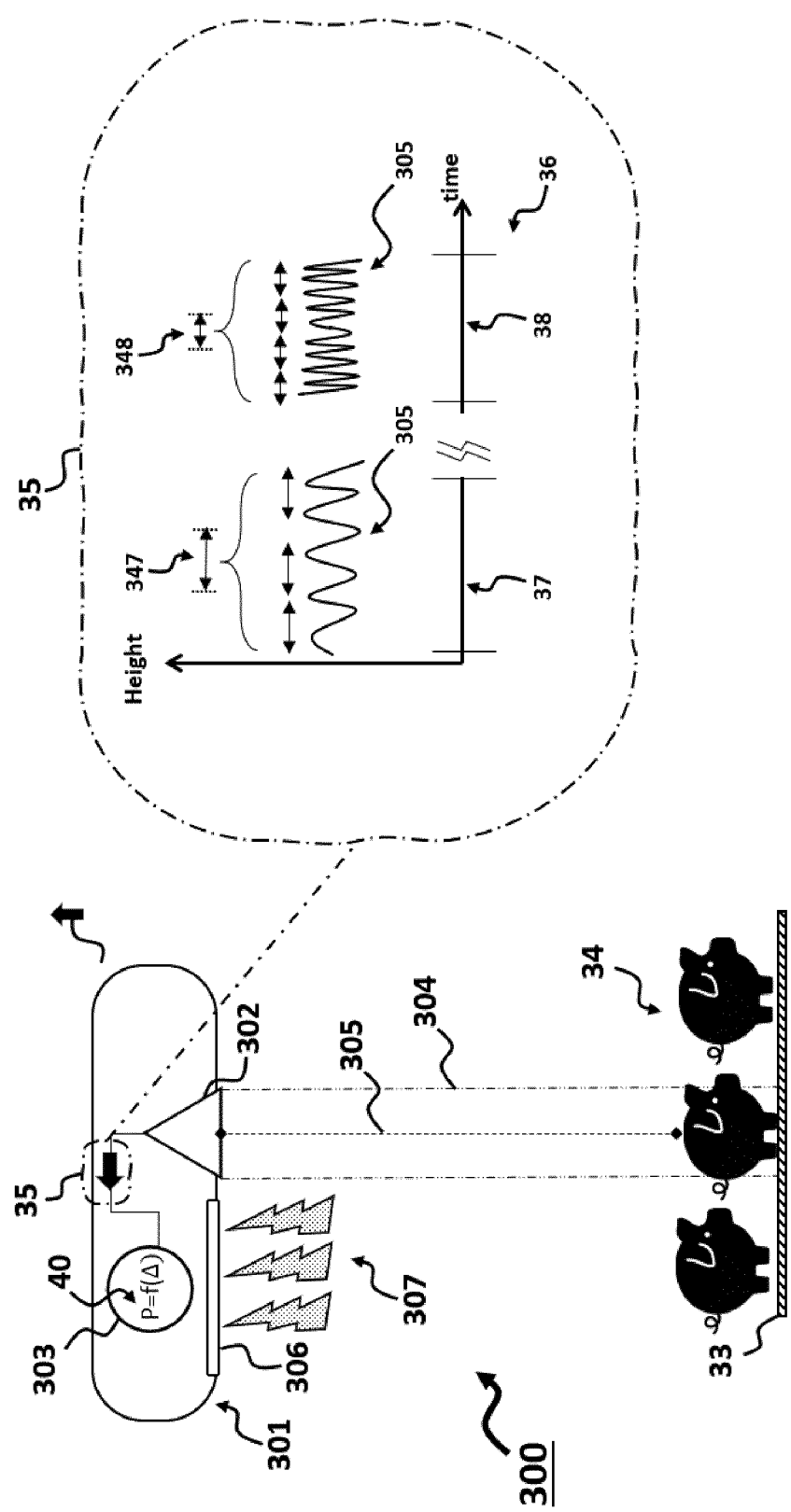
FIG. 3 depicts schematically an embodiment of a lighting system according to the invention.

FIG. 3 depicts, by non-limiting example, schematically an embodiment of a lighting system 300 according to the invention. The lighting system 300 comprises a sensing system according to the invention. Namely, the lighting system 300 comprises a luminaire 301. The luminaire 301 comprises a controller 303, a light source 306, and a range sensor 302. Here, the controller 303 is comprised by the luminaire 301. The range sensor 302 has a Field-of-View 304 to a surface area 33. The surface area 33 is part of a stable for pigs. Hence, a group of pigs 34 are present on the surface area 33. The light source 306 is arranged for illuminating the surface area 33 with a lighting characteristic 307.

Alternatively, the group of pigs may be a single pig, or a set of animals as mentioned before in the present application. Alternatively, the range sensor may be at least one range sensor, for example the lighting system may comprise a plurality of luminaires (such as an array) each comprising a respective range sensor of the at least one range sensor. Alternatively, the controller may be located external to the luminaire, such as a central controller, for example a central controller operatively coupled to multiple luminaires. The light source may be controlled by the (same) controller.

Referring to FIG. 3, the range sensor 302 measures at least continually, but preferably continuously, the heights 305 of the pigs of the group of pigs 34 passing the Field-of-View 304 during a period of time 36. The Field-of-View 304 is arranged such that substantially only one pig at a time may occupy the Field-of-View 304. The range sensor 302 is a single-pixel optical Time-of-Flight sensor, but may alternatively be a multi-pixel Time-of-Flight sensor, an infrared range sensor, a FMCW radar sensor, an ultrasound range sensor.

The range sensor 302 provides the measured heights 305 of pigs of the group of pigs 34 during the period of time 36 to the controller 303. Namely, the range sensor 302 provides a height signal 35 comprising the measured heights 305 during the period of time 36 to the controller 303. The controller 303 obtains the height signal 35 and processes the height signal 35. The controller 303 thereby determines a parameter 40 of the group of pigs 34 based on the measured heights 305 during the period of time 36.

More specifically, in the present embodiment, the parameter 40 is an activity parameter. The activity parameter is the type of locomotion of the pigs. The activity parameter 40 is correlated to the duration of the measured heights 305 of the group of pigs 34. Namely, the controller determines the type of locomotion of the group of pigs 34 by comparing an average duration 348 of the measured heights 305 of pigs of the group of pigs 34 during a second subperiod of time 38 with an average duration 347 of the measured heights 305 of pigs of the group of pigs 34 during a first subperiod of time 37.

As depicted in FIG. 3, the average duration 348 of the measured heights 305 of pigs of the group of pigs 34 during the second subperiod of time 38 is shorter than the average duration 347 of the measured heights 305 of pigs of the group of pigs 34 during the first subperiod of time 37. This means that the pigs of the group of pigs 34 are on average moving faster in the second subperiod of time 38 compared to the first subperiod of time 37. A similar principle on how to determine an increment in velocity is explained in the subject-matter related to FIG. 2.

Hence, considering the height signal 35, the controller 303 concludes that the group of pigs 34 has on average (as a group) an increased locomotion and/or motion. This increased locomotion and/or motion may be indicative of (or correlated to) the type of locomotion being changed from walking to running. This change in type of locomotion may indicate overall stress in the group of pigs 34.

Still referring to FIG. 3, upon the controller 303 determining the activity parameter 40, the controller 303 controls the light source 306 of the lighting device 301 to provide a lighting characteristic 307 based on the activity parameter 40. Here, the lighting characteristic is a reduced light intensity and soothing light scene, so as to calm the group of pigs 34, since the group of pigs 34 is determined to be in stress due to their on average faster movement and/or locomotion.

Alternatively, said lighting device may be another electrical device, such as e.g. a speaker, a HVAC device, a fodder device, a watering device, a scent diffuser, a fan, an electric door, a heater device, a cooler device. Such devices may also provide calming effects to the group of pigs. The electrical device may also be e.g. a radiofrequency emitting device, a user interface device, a cloud, a server device. Such devices may convey a notification signal to a stable responsible or farm owner.

Figure 4:
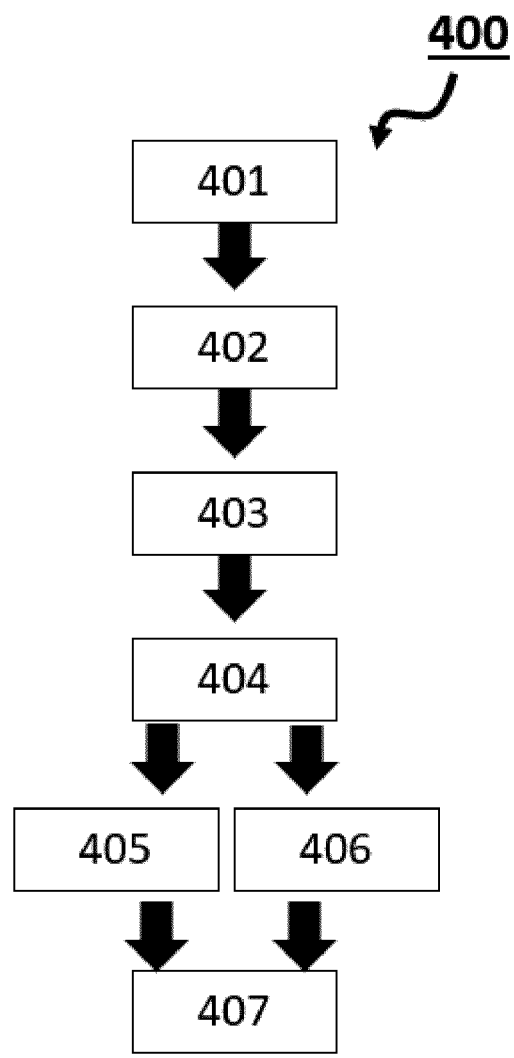
FIG. 4 depicts schematically an embodiment of a method according to the invention.

FIG. 4 depicts schematically, by non-limiting example, an embodiment of a method 400 of determining a parameter of a set of animals present on a surface area. The method is performed by a range sensor and a controller according to the invention, which may be part of a sensing system or a lighting system, or a lighting device. The method may alternatively be performed for a single animal present on a surface area. The method 400 comprises the step 401 of at least continually (e.g. continuously) measuring heights of animals of the set of animals passing a Field-of-View of a range sensor during a period of time. The method 400 comprises a step 402 of providing, from the range sensor to the controller, a height signal comprising said measured heights during the period of time. Said providing may alternatively be conveying. The method comprises a step 403 of the controller obtaining said height signal. Said obtaining may be either via the controller receiving or retrieving said height signal. For example, the height signal may be conveyed to the controller via an intermediate device, such as a cloud. The method further comprises the step 404 of the controller determining the parameter of the set of animals based on the measured heights during the period of time.

The parameter may be a growth parameter. The growth parameter is correlated to the measured heights of the set of animals. Therefore, the method comprises the step 405 of determining the growth parameter by comparing an average of the measured heights of the animals of the set of animals during a second subperiod of time with an average of the measured heights of the animals of the set of animals during a first subperiod of time. However, the parameter may also be an activity parameter. The activity parameter is correlated to the duration of the measured heights of the set of animals. Therefore, the method may alternatively or additionally comprise the step 406 of determining the activity parameter of the set of animals by comparing an average duration of the measured heights of the animals of the set of animals during a second subperiod of time with an average duration of the measured heights of the animals of the set of animals during a first subperiod of time.

In further embodiments, also depicted in FIG. 4, the method according to the invention may further comprises the step 407 of controlling an electric device upon determining said parameter above. For example, the electric device may be a lighting device of which a lighting characteristic is controlled.

The invention claimed is:

1. A sensing system for determining a parameter of a set of animals present on a surface area, wherein the sensing system comprises:
 a controller; and
 at least one range sensor having a Field-of-View configured to be directed to the surface area;
 wherein each range sensor of the at least one range sensor comprises a single pixel configured to at least continually measure heights of animals of the set of animals passing the Field-of-View during a period of time, and to provide a height signal comprising said measured heights during the period of time;
 wherein the controller is configured to obtain said height signal, and to determine the parameter of the set of animals based on the measured heights during the period of time;
 wherein the parameter is an activity parameter of the set of animals;
 wherein the activity parameter is correlated to the duration of the measured heights of the set of animals, the duration indicating how long a measured height of the measure heights of the set lasts in time during the period of time;
 wherein the controller is configured to determine the activity parameter of the set of animals by comparing an average duration of the measured heights of the animals of the set of animals during a second subperiod of time with an average duration of the measured heights of the animals of the set of animals during a first subperiod of time.

2. The sensing system according to claim 1,
 wherein the parameter is a growth parameter;
 wherein the growth parameter is correlated to the measured heights of the set of animals;
 wherein the controller is configured to determine the growth parameter by comparing an average of the measured heights of the animals of the set of animals during a second subperiod of time with an average of the measured heights of the animals of the set of animals during a first subperiod of time.

3. The sensing system according to claim 2, wherein the growth parameter is at least one of:
an average increment of the height of the set of animals, an average increment of the size of the set of animals, or an average increment of the weight of the set of animals.

4. The sensing system according to claim 1, wherein the activity parameter is at least one of:
an activity of the set of animals,
a rate of locomotion of the set of animals, or
a type of locomotion of the set of animals.

5. The sensing system according to claim 4,
wherein the activity of the set of animals comprises one of: sleeping, resting, eating or moving; or
wherein the type of locomotion of the set of animals comprises one of: sitting, walking, running, laying, or having stress.

6. The sensing system according to claim 1, wherein the set of animals is one of: a flock of chicken, a herd of livestock, a group of pigs, a colony of terrestrial insects.

7. The sensing system according to claim 1,
wherein the sensing system comprises an array of electric devices;
wherein each electric device of the array of electric devices comprises a respective range sensor of the at least one range sensor.

8. The sensing system according to claim 7, wherein the array of electric devices comprises an array of lighting devices.

9. The sensing system according to claim 1, wherein the controller is configured to control an electric device upon determining the parameter.

10. The sensing system according to claim 1, wherein the at least one range sensor is one of: a single-pixel Time-of-Flight sensor, an infrared range sensor, a LIDAR.

11. The sensing system according to claim 1, wherein the surface area comprises a feeding area, wherein the Field-of-View of a range sensor of the at least one range sensor is configured to be directed to the feeding area.

12. A method of determining a parameter of a set of animals present on a surface area, wherein the method comprises:
at least continually measuring heights of animals of the set of animals passing a Field-of-View of a range sensor comprising a single pixel during a period of time;
the range sensor providing a height signal comprising said measured heights during the period of time; and
a controller obtaining said height signal and determining the parameter of the set of animals based on the measured heights during the period of time;
wherein the parameter is an activity parameter;
wherein the activity parameter is correlated to the duration of the measured heights of the set of animals;
wherein the method comprises:
determining the activity parameter of the set of animals by comparing an average duration of the measured heights of the animals of the set of animals during a second subperiod of time with an average duration of the measured heights of the animals of the set of animals during a first subperiod of time, the average duration indicating how long a measured height of the measure heights of the set lasts in time during the period of time.

13. The method according to claim 12,
wherein the parameter is a growth parameter;
wherein the growth parameter is correlated to the measured heights of the set of animals;
wherein the method comprises:
determining the growth parameter by comparing an average of the measured heights of the animals of the set of animals during a second subperiod of time with an average of the measured heights of the animals of the set of animals during a first subperiod of time.

* * * * *